United States Patent [19]

Anderson et al.

[11] Patent Number: 4,463,764
[45] Date of Patent: Aug. 7, 1984

[54] CARDIOPULMONARY EXERCISE SYSTEM

[75] Inventors: Stephen T. Anderson; Catherine A. Anderson, both of Stillwater; Terrance J. Kapsen, Minneapolis, all of Minn.

[73] Assignee: Medical Graphics Corporation, Shoreview, Minn.

[21] Appl. No.: 306,607

[22] Filed: Sep. 29, 1981

[51] Int. Cl.³ ............................................. A61B 5/08
[52] U.S. Cl. ................................... 128/719; 128/725; 128/671
[58] Field of Search ............... 128/670, 671, 707, 716, 128/717, 718, 719, 725; 273/DIG. 5, DIG. 6; 364/413, 415, 417

[56] References Cited

U.S. PATENT DOCUMENTS 4,296,756 10/1981 Dunning et al. .................... 128/716

OTHER PUBLICATIONS

Miyamoto et al., "Online Computer for Assessing Respiratory and Metabolic Function During Exercise", Medical and Biological Engineering and Computing, May 1981; pp. 340–348.
Howard et al., "Computerized Cardiopulmonary Stress Testing in Children", IEEE, 1979.

Primary Examiner—Kyle L. Howell
Assistant Examiner—Francis J. Jaworski
Attorney, Agent, or Firm—Orrin M. Haugen; Thomas J. Nikolai; Douglas L. Tschida

[57] ABSTRACT

A cardiopulmonary exercise system for real-time, breath-by-breath acquisition, analysis, display and printing of an individual's physiologic parameters. A microprocessor based waveform analyzer receives inputs from a $CO_2$ analyzer, an ECG monitor, an $O_2$ analyzer, and a pneumotachograph, and, optionally, can also connect a cycle ergometer, a treadmill, a cardiac stress system, and an ear oximeter. The waveform analyzer provides output data to a host central processor unit to which a CRT display, a graphics copier or hard-copy printer may be connected for providing medical data for assessment of an individual's heart and lungs, on a real-time basis whereby the level of fitness or underlying organic defects which may effect the cardiopulmonary system can be determined. The pneumotachograph, $CO_2$ analyzer and $O_2$ analyzer and ECG monitor provide analog signals representing flow, $CO_2$ and $O_2$ levels in expired air as well as heart rate. The waveform analyzer, under control of its dedicated microprocessor, performs an A/D conversion with the microprocessor also being used to calculate the tidal volume ($V_T$), minute ventilation ($V_E$), breathing frequency ($f_B$), cardiac frequency ($f_C$), inspiratory time ($T_I$) and total time ($T_{TOT}$) of last breath, fraction of $CO_2$ in inspired gas ($F_{ICO2}$) and fraction of $O_2$ in inspired gas ($F_{IO2}$), peak $CO_2$ and $O_2$ ($F_{ETCO2}$ and $F_{ETO2}$), and expired volumes of $CO_2$ and $O_2$ ($VCO_2$ and $VO_2$) breath-by-breath. The system of the preferred embodiment analyzes the individual's expirate at a sample rate of one hundred samples per second per channel with twelve bit resolution.

6 Claims, 14 Drawing Figures

CURT   28-AUG-81                CARDIOPULMONARY EXERCISE TEST
INTERVAL 4   WORK LOAD 450
             SYSTOLIC: 4   DIASTOLIC: 4

| SECS | VT | RR | V̇E | PETO2 | PETCO2 | V̇O2 | V̇CO2 | R | V̇E/V̇O2 | V̇E/V̇CO2 | HR | V̇O2/HR | SAT |
|---|---|---|---|---|---|---|---|---|---|---|---|---|---|
| 252 | 1573 | 17 | 22 | 97.6 | 43.8 | 903 | 822 | 0.91 | 18 | 19 | 115 | 7.9 | 97 |
| 254 | 1233 | 26 | 27 | 97.6 | 43.8 | 957 | 861 | 0.90 | 20 | 22 | 116 | 8.2 | 97 |
| 256 | 1135 | 33 | 31 | 97.9 | 43.1 | 1104 | 954 | 0.86 | 19 | 22 | 117 | 9.4 | 97 |
| 262 | 2171 | 11 | 20 | 90.7 | 48.2 | 970 | 877 | 0.90 | 15 | 17 | 118 | 8.2 | 98 |
| 264 | 1172 | 27 | 26 | 91.4 | 47.9 | 1068 | 863 | 0.81 | 17 | 21 | 118 | 9.0 | 98 |
| 267 | 1898 | 17 | 27 | 94.1 | 44.8 | 1200 | 1062 | 0.88 | 17 | 19 | 119 | 10.1 | 98 |
| 270 | 1456 | 25 | 30 | 94.5 | 44.8 | 1242 | 1043 | 0.84 | 17 | 21 | 120 | 10.4 | 98 |
| 272 | 1551 | 23 | 29 | 94.1 | 44.8 | 1209 | 1033 | 0.85 | 17 | 20 | 120 | 10.1 | 98 |
| 275 | 1586 | 22 | 29 | 95.8 | 43.8 | 1167 | 1036 | 0.89 | 18 | 20 | 121 | 9.6 | 98 |
| 278 | 1726 | 18 | 26 | 95.8 | 45.1 | 1144 | 1058 | 0.92 | 17 | 18 | 122 | 9.4 | 98 |
| 280 | 1377 | 30 | 34 | 96.2 | 44.8 | 1294 | 1103 | 0.85 | 19 | 22 | 122 | 10.6 | 98 |
| 283 | 1866 | 21 | 32 | 93.1 | 46.9 | 1423 | 1282 | 0.90 | 17 | 19 | 123 | 11.6 | 97 |
| 288 | 2949 | 12 | 28 | 93.4 | 46.9 | 1225 | 1159 | 0.95 | 18 | 19 | 124 | 9.9 | 97 |
| 291 | 1634 | 21 | 29 | 95.1 | 46.2 | 1206 | 1069 | 0.89 | 17 | 19 | 123 | 9.9 | 97 |
| 295 | 2170 | 16 | 28 | 94.1 | 46.9 | 1224 | 1146 | 0.94 | 17 | 18 | 123 | 9.9 | 97 |
| 297 | 1455 | 24 | 29 | 93.1 | 47.5 | 1219 | 1087 | 0.89 | 17 | 19 | 123 | 9.9 | 97 |
| 301 | 2305 | 19 | 36 | 93.8 | 46.5 | 1474 | 1382 | 0.94 | 18 | 19 | 124 | 11.9 | 97 |

FIG. 6

CARDIOPULMONARY EXERCISE SYSTEM

CROSS REFERENCES TO CO-PENDING APPLICATIONS

This application relates to patent application Ser. No. 165,949, filed July 3, 1980, now abandoned; inventors Stephen T. and Catherine A. Anderson, which is assigned to Medical Graphic Corporation, the same assignee as this patent application.

BACKGROUND OF THE INVENTION

1. Field of the Invention

This invention relates to an electronic medical instrumentation system and, more specifically, pertains to a real time breath-by-breath cardiopulmonary exercise system for assessing the performance of the heart and lungs during exercise.

2. Description of the Prior Art

Prior art exercise monitors and systems have failed to provide a breath-by-breath analysis of an individual's heart and lungs during exercise.

The earliest prior art exercise monitors involved an individual's exhaling or expiring into a bag, such as a Douglas bag or weather balloon, for manual collection of expired gases. A laboratory technician would then, at the end of an exercise period, use a gas analyzer to analyze the gases in the bag to determine the expired $CO_2$ and $O_2$. Further, analysis of expired volume involved dumping the bag contents into a gasometer (Tissot) and quantifying the volume of gas expired during the collection period. From this raw data, numerous hand calculation were required in order to determine a few of the possible cardiopulmonary parameters.

Another prior art device is a mixing chamber which is used to gather an individual's expired breath and is spot sampled by gas analyzers at periodic intervals to determine an average expired gas concentration. Expired volume is measured by either the bag method previously described or by another volume transducing device such as a turbine.

All of the prior art devices fail to provide a breath-by-breath analysis to resolve the important first breaths of expiration during an exercise period. The prior art devices fail to account for minute intervals typically present in disability and rehabilitation evaluations. Hence, a base line for standard assessment of that individual's performance and parameters of the heart and lungs is not made available.

The cardiopulmonary exercise system of the present invention is a real-time distributed processing system which analyzes each breath, begining with the first breath and continuing over a specified time interval, and allows the monitoring of an individual either while at rest or during stress.

SUMMARY OF THE INVENTION

The present invention provides a cardiopulmonary exercise system including a microprocessor based waveform analyzer for performing in real time a breath-by-breath analysis of heart-lung activity of an individual at rest or, more importantly, during a stress exercise period, for measurement of a plurality of parameters. The system can be utilized to ascertain an organic heart or lung problem, or to generally assess an individual's physical fitness. The system is a dedicated, user-access diagnostic system providing an output of an individual's basic metabolic function on a breath-by-breath basis or over a user-specified time interval, beginning with the first breath and continuing for as long as the individual exercises in a stress condition or is monitored while in a rest condition.

According to the preferred embodiment of the present invention, there is provided a microprocessor based waveform analyzer coupled to receive as inputs the outputs from cardiopulmonary transducers for yielding a real-time, breath-by-breath analysis of an individual's cardiopulmonary parameters. For example, the inputs may include a pneumotachograph, an $O_2$ analyzer, a $CO_2$ analyzer, an ECG monitor, and, if desired, an optional cycle ergometer, a treadmill, other types of cardiac stress systems, and an ear oximeter. The waveform analyzer, operating under computer control, samples and converts the analog signals from the transducers to digital signals while simultaneously compensating for phase shifts of the signals and storing them for subsequent computations. The waveform analyzer is configured to transmit digital data defining an individual's heart/lung parameters for recording on tape or disk, or for graphic display on a CRT, and to a hard-copy printer under control of a host computer. Such parameters as tidal volume, minute ventilation, breathing frequency, cardiac frequency, inspiratory time of last breath, total time of a preceding breath, minimum $CO_2$ and $O_2$, peak $CO_2$ and $O_2$, and volume of $CO_2$ and $O_2$ can be stored, displayed or recorded. The system provides for real-time monitoring of a patient while under stress conditions until the anaerobic threshold is reached. When the stress is then removed, the recovery of the cardiopulmonary functions can be observed. In that the monitoring is performed on a breath-by-breath basis, unnecessary patient effort and risk is eliminated which becomes important when the patient is undergoing cardiac or pulmonary rehabilitation.

The sampling may occur, for example, one hundred times per second on each dynamic channel to thereby provide for a relatively continuous, update of information being processed by the waveform analyzer. The waveform analyzer is uniquely controlled so as not only to account for each breath, but also for detection of inconsistent breathing patterns, such as may be the result of coughing, swallowing, etc.

Another significant feature of the present invention is the inclusion in a cardiopulmonary exercise system of means whereby fitness problems or organic heart and lung disease can be diagnosed and monitored during the treatment and rehabilitation programs. The system comprises a single dedicated electronic assembly providing for instantaneous display of an individual's cardiopulmonary parameters either in a graphical display or in tabularized data format on a breath-by-breath basis. The printed output may later be used to expedite reimbursement of medical costs, whether the reimbursement is by way of insurance carrier or the government medical reimbursement program.

An additional significant aspect and feature of the present invention is a cardiopulmonary exercise system for conducting stress testing. The patient may be made to use a cycle ergometer, a treadmill or some other device to perform work and while so working, certain metabolic parameters such an anaerobic threshold may be determined. As such, the patient can be restrained so as not to exceed a predetermined safe threshold. This is particularly important for those individuals who are being diagnosed for medical conditions, thereby eliminating unnecessary patient effort and discomfort, especially for those cases where exercise could be considered to involve risk to the patient.

A further significant aspect and feature of the present invention is a breath-by-breath analysis of gas exchange for exercise testing in a clinical environment, allowing for rapidly advancing incremental exercise tests. Complete information about the patient's anaerobic parameters can be obtained using an incremental or ramp exercise study. This type of rapidly advancing exercise tests results in minimal patient fatigue and rapid recovery following cessation of exercise. This is advantageous in that repeated testing can be utilized for evaluating the effect of a drug or oxygen treatment on the body's response to exercise.

Having thus described certain features of the preferred embodiment of the present invention, it is a principal object hereof to provide a cardiopulmonary exercise system providing real-time, breath-by-breath analysis for monitoring of an individual, whether that individual be at rest or in a stress test.

A further object of the present invention is a cardiopulmonary exercise system which includes flexibility in clinical utilization, patient safety and convenience, increased resolution and accuracy in the measurement of maximum oxygen uptake ($VO_2$ max), the ability to measure the kinetics of $O_2$ uptake, $CO_2$ output, and ventilation during exercise, the ability to measure and trend end tidal gas values during the entire exercise test, and also reduce time in performing, reporting, and recording, by way of hard copy, an exercise test.

Yet another object of the present invention is to provide a cardiopulmonary testing apparatus utilizing plural data processors operating on a coordinated basis through a prescribed allocation of tasks between distributed processors. Specifically, a first processor is used to control the sampling of various metabolic parameters, convert the sampled values to digital representations thereof and perform various computations using the digital data. A second processor is used in conjunction with printing, plotting and display equipment to provide meaningful data to the user.

Another object of the present invention is to provide a cardiopulmonary exercise system which includes a waveform analyzer providing for the sampling of a plurality of analog inut parameters, the waveform analyzer including circuitry for converting the analog signals into digital signals, and for adjusting the phase shift of the dynamic signals pertaining to $O_2$ and $CO_2$ concentration so that they will be properly aligned timewise so as to be correlated with flow. That is, the waveform analyzer also includes circuitry for digitizing the inspiratory and expiratory flow, storing those signals and correcting for the phase lag between the flow expiration signals and the $O_2$ and $CO_2$ signals.

A further object of the present invention is a cardiopulmonary exercise system which provides for real-time display or plotting, on a breath-by-breath basis, of a plurality of parameters, including tidal volume, respiratory rate, expired ventilation, partial pressure end tidal $O_2$, partial pressure end tidal $CO_2$, $O_2$ uptake, $CO_2$ output, respiratory quotient, ventilatory equivalent for $O_2$, ventilatory equivalent for $CO_2$, heart rate, $O_2$ pulse and $O_2$ saturation. These parameters are not to be construed as limiting of the parameters of the present invention, and are by way of example and for purposes of illustration only.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein.

DESCRIPTION OF PREFERRED EMBODIMENTS

Figure 1:
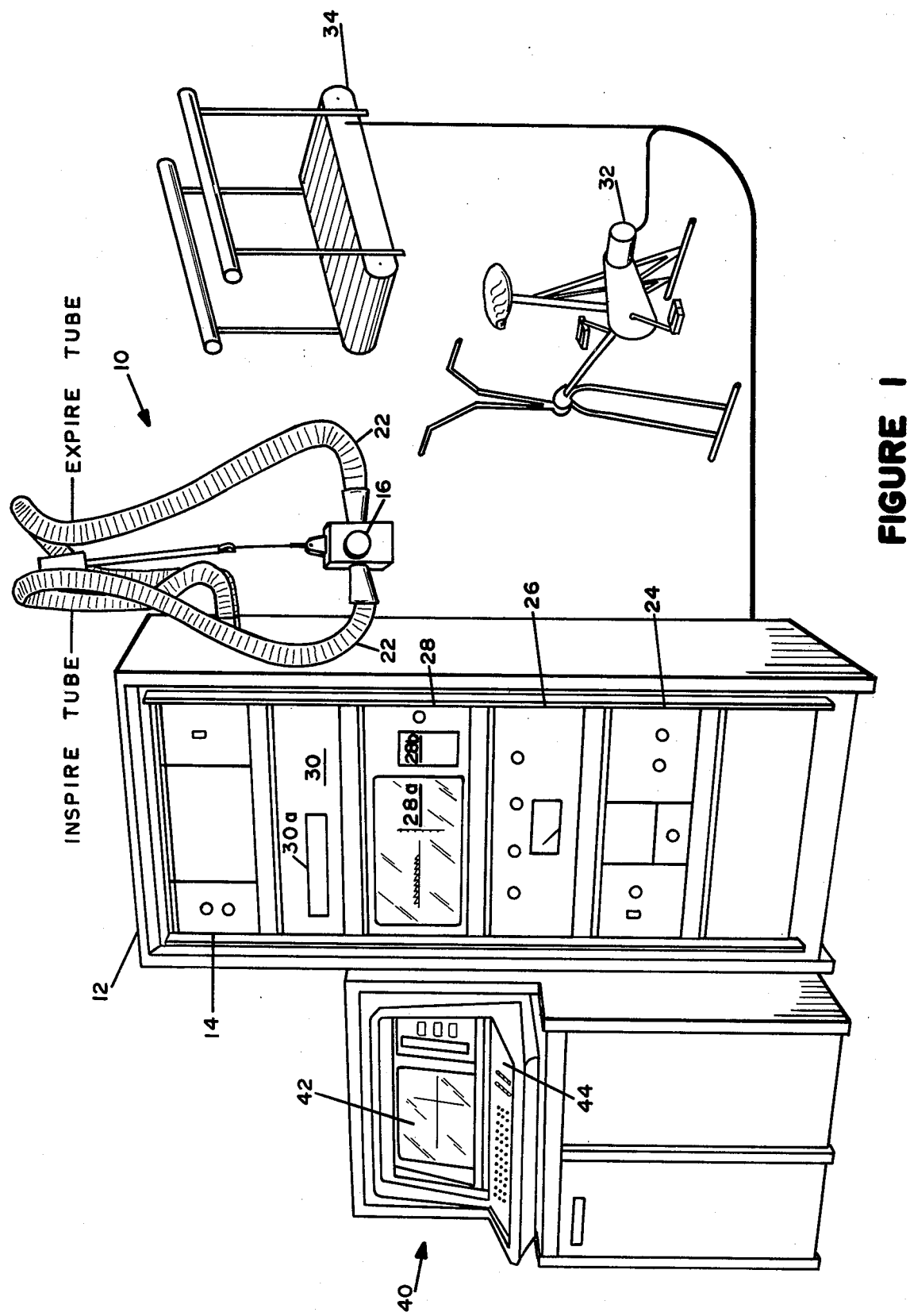
FIG. 1 illustrates a perspective view of a preferred embodiment of the cardiopulmonary exercise system of the present invention.
Figure 2:
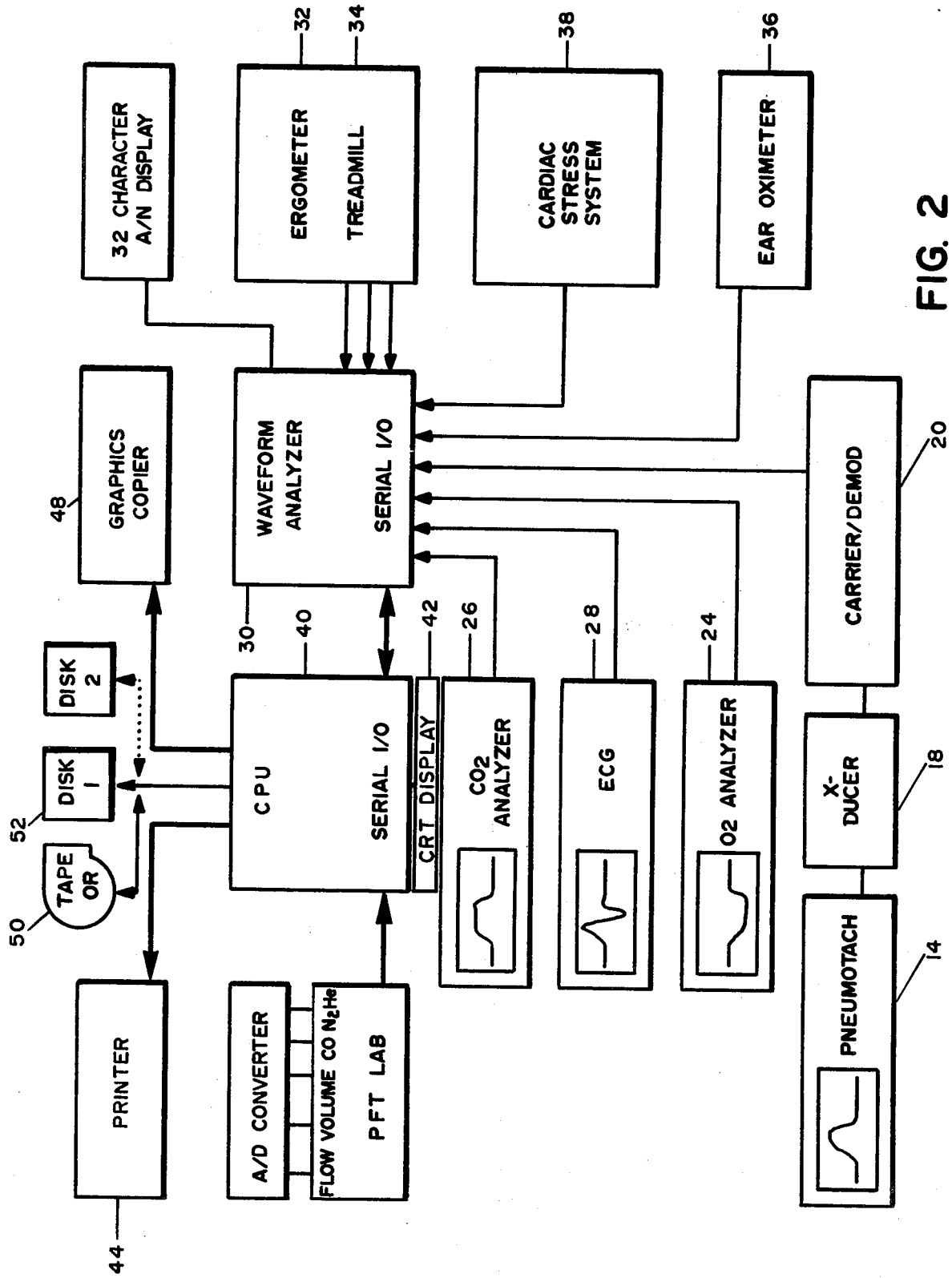
FIG. 2 illustrates a block diagram of the system.

Referring to FIGS. 1 and 2 which respectively show a perspective view of the hardware components, comprising the preferred embodiment of the exercise system 10 and a system block diagram of same, there can be seen an equipment rack or frame 12 which contains a plurality of modules including a pneumotachograph 14 which is coupled to a mouthpiece 16. Proximate the mouthpiece 16 is a differential pressure transducer 18 and an associated carrier-demodulator amplifier 20 used to provide an analog electrical signal proportional to gas flow during breath inspiration and expiration. Since various forms of pneumotachs are commercially available, it is not deemed necessary to explain herein the constructional details of that unit. As shown in FIG. 1, a set of flow tubes 22 are also coupled between the mouthpiece 16 and lead to an oxygen ($O_2$) analyzer 24 and a carbon dioxide ($CO_2$) analyzer 26.

An ECG monitor-recorder 28 with a CRT display 28a and a strip recorder 28b provide for ECG output of an individual. A waveform analyzer 30, as later described in FIGS. 2 and 3, connects to the pneumotach 14, the ECG monitor-recorder 28, the $O_2$ analyzer 24, and the $CO_2$ analyzer 26. The waveform analyzer 30 may also connect to a cycle ergometer 32, a treadmill 34, an optional ear oximeter 36, and a cardiac stress system 38. System components 24 through 38 are available and known in the art and are accordingly connected to the waveform analyzer 30, as later described in detail. A further equipment rack includes a central processor unit 40 a cathode ray tube display 42, a teletypewriter key-board 44, a graphics copier 48, a tape drive 50, and an optional disk 52 as illustrated diagrammatically in FIG. 2.

The inspire and expire tubes 22, the mouthpiece assembly 16, and transport tubing for the $O_2$ analyzer 24 and $CO_2$ analyzer 26 are supported by two-bar linkage from the equipment rack 12 so that the person under test can comfortably maintain the mouthpiece in his mouth. The system 10 allows for precise, accurate breath-by-breath measurement of respiratory and cardiac functions in addition to sampling of expired gases from the individual's respiratory system.

FIG. 2 is a block diagram representation of the cardiopulmonary exercise system 10 showing the relative interconnection of the various components 14 through 52, all of which are described in detail hereinbelow. The waveform analyzer is shown diagrammatically in FIG. 3 and has a plurality of serial input-output channels for system input and output devices 14 through 38. The waveform analyzer 30 connects to the computer 40.

The pressure transducer 18 (FIG. 2) functions to convert the differential pressures obtained during inspiration and expiration of breath through the mouthpiece 16 to electrical signals which are directly proportional to the respiratory gas flow. This electrical signal is applied to a first input channel (CH 1) of the waveform analyzer 30.

A sample tube (not shown) connects from the mouthpiece 16 to the inputs of a $CO_2$ analyzer 26. The analyzer 26 may be one of a number of commercially available devices which is designed to measure the concentration of carbon dioxide in an expiratory gas mixture by utilizing infrared absorption techniques. It is understood, however, that other types of devices are available for measuring $CO_2$ partial pressures in a gas mixture and, hence, the invention should not be construed to be limited to the use of the infrared absorption type of $CO_2$ analyzer. The output from the analyzer 26 is an electrical analog waveform corresponding to real time $CO_2$ concentration during the monitored respiratory cycles. This electrical signal is applied to a second input channel of the waveform analyzer 30.

In the same manner as described above, expiratory gas passes from the mouthpiece 16 to the inlet port of an $O_2$ analyzer 24 which, too, provides an electrical output that is a measure of the partial pressure of oxygen in the gas mixture being sampled. This electrical signal is applied to a third input channel of the waveform analyzer 30.

Figure 3:
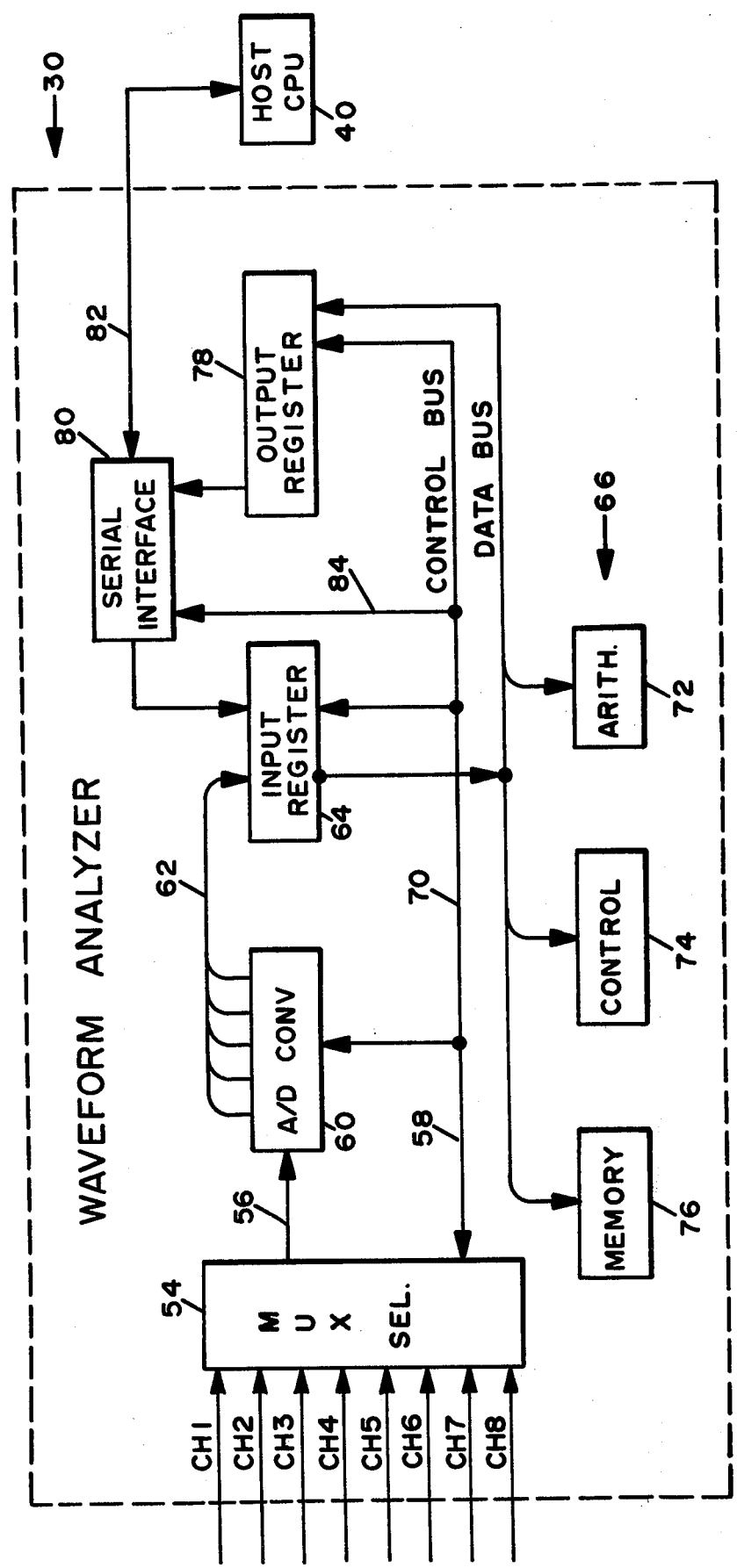
FIG. 3 illustrates a schematic block diagram of a waveform analyzer used in the system of FIGS. 1 and 2.

As shown by FIG. 3 the waveform analyzer 30 is preferably a microprocessor based system for analyzing analog waveforms and which is programmed to compare received waveforms with a predetermined standard, such that those waves not conforming to the standard will be eliminated from further processing operations. In this regard, the waveform analyzer may be capable of measuring and storing values corresponding to the peaks of a received waveform and the frequency of the incoming signals. Provision is also made in the waveform analyzer to allow it to be under control of an external device, such as the host CPU40 which may be a general purpose digital computer. The waveform analyzer 30 is provided with a serial interface. By including a microprocessor type control in the waveform analyzer 30, it is possible to program the unit whereby a variety of inputs may be analyzed and specific tasks performed on the data in a desired sequence.

There are four analog waveforms typically brought in on channels 1, 2, 3 and 4 of the waveform analyzer 30 which are respectively proportional to gas flow, carbon dioxide and oxygen levels in the expiratory gas mixture and heart rate. The heart rate signal is conveniently obtained from the ECG 28 and is applied to channel 4 of the waveform analyzer 30. Based upon these input signals, in addition to others as predetermined, the waveform analyzer 30 is arranged to process the received data to yield such parameters as end tidal volume, ventilation, inspiratory time of last breath, the total time of the last breath, breathing frequency, etc. Utilizing the analog waveform from the carbon dioxide analyzer 26, the waveform analyzer can be programmed to compute the $CO_2$ peak value, baseline value as well as the volume of $CO_2$ expired in the last breath. Likewise, the analog signal obtained from the oxygen analyzer 24 can be processed within the waveform analyzer 30 to yield values indicative of the peak $O_2$, baseline $O_2$, and the volume of $O_2$ expired in the preceding breath. The heart rate signal applied to channel 4 of the waveform analyzer is merely the heart rate measured in beats per unit of time.

The serial digital data from the waveform analyzer 30 may be applied through a serial interface to the computer 40 which is programmed to perform various computations on the received data. The computer may, for example, compute for each breath, the ventilation value in liters per minute and present the computed result to video display terminal 42 or to a printer/plotter. In addition, the computer 40 can be programmed to provide an instantaneous display on the CRT display screen 42 of a series of text-type instructions, providing prompts to a medical technologist so that the system will be properly calibrated and used. That is, the video display 42 can also present a sequential indication of the steps to be followed in performing the initial calibrations and the later patient testing functions. As such, the computer and display capability makes the system "interactive," thereby lessening the need for highly trained operating personnel.

Referring again to FIG. 3, the waveform analyzer 30 includes an analog input multiplexer 54 having a plurality of input channels, e.g., CH. 1-CH.8, to which the flow measuring apparatus 14, 18 and 20, the gas analyzer apparatus 24 and 26, and the ECG monitor 28 are connected. The multiplexer functions in a conventional fashion to individually couple any one of the channels at a time to an output line 56 depending upon the signals applied to the selector inputs 58 of the multiplexer from its internal microprocessor. The output line 56 is coupled to an input of an analog-to-digital converter 60 which operates in a known fashion to generate a binary code pattern or word on the parallel output lines 62 which is indicative of the analog signal applied at its input.

The output from the A/D converter 60 is coupled to an input register 64 of a bus structured microprocessor 66. The microprocessor includes a data bus 68 and a control bus 70 along with an arithmetic module 72, a control module 74 and a memory module 76. Each of the modules receives control signals via the control bus 70 and to transmit or receive operand information via the data bus 70. As such, information from the input register 64 is transferred via the data bus 68 to the memory 76 under control of the control module 74. Alternatively, data may be transferred between the memory module 76 and the arithmetic module 72 via the data bus 68.

Data from the memory 76, the arithmetic unit 72 or the control module 74 can also be transferred via the data bus 68 to an output register 78. Where a serial data transmission is desired, the output register 78 may have its individual stages applied to a parallel to serial converter contained in the serial interface 80 and the serial output therefrom on line 82 may be clocked out at a rate determined by control signals applied via the control bus to the serial interface clock input 84. The data from the waveform analyzer 30 can be transmitted upon the completion of each breath or by specifying a user selected time interval of up to 60 seconds, to the host computer 40 which is used to control a CRT display 42 or a hard copy printerplotter device 44 as illustrated in FIG. 2.

PREFERRED MODE OF OPERATION

The operation of the cardiopulmonary exercise system 10 is best described with reference initially made to FIG. 4.

Figure 4:
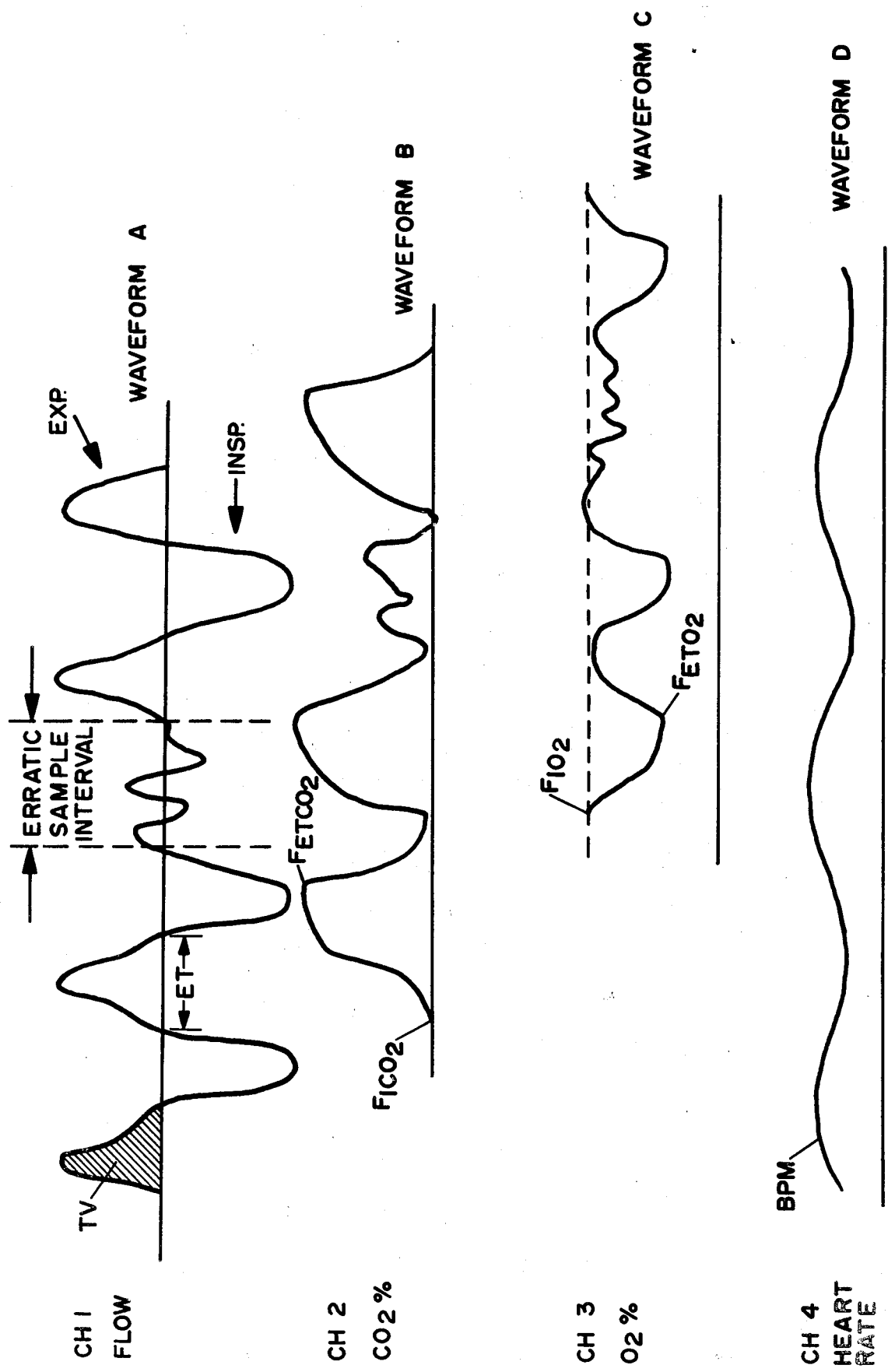
FIG. 4 illustrates representative waveform inputs to the waveform analyzer of FIGS. 2 and 3.

FIG. 4 illustrates representative waveform inputs to the waveform analyzer 30 of FIGS. 1 through 3, particularly FIGS. 2 and 3. The figure shows the four input analog signals from the carrier/demodulator 20 associated with the pneumotach 14, the $CO_2$ analyzer 26, the $O_2$ analyzer 24, and the ECG 28. Three dynamic channels allow sampling to take place at a rate of about one hundred samples per second per channel.

In operation, the patient or individual to be tested in either a rest or a stress mode will place the mouthpiece 16 into his or her mouth for the real time breath-by-breath analysis. Of course, prior to operation, the pneumotach 14, analyzers 24 and 26, and ECG have been initially calibrated and adjusted.

The signal appearing at the output of the (carrier/demodulator) amplifier 20 during any one of the plural sampling periods is represented by waveform "A", which constitutes the instantaneous flow of the patient's respiratory system measured in milliliters per minute. It is noted that for the most part, the flow waveform is quite rhythmical but in the segment bracketed by the vertical dashed lines, the pattern becomes somewhat erratic before again resuming the rhythmical pattern. The erratic portion of the curve may occur due to a cough or a sneeze or the like.

As is more fully explained, the waveform analyzer 30 operates to eliminate from the various measurements to be plotted any data which would otherwise be based on the erratic portion of the respiratory flow. The waveform analyzer 30 is capable of detecting frequency variations of a received signal from a norm and to create an inhibit condition whereby computations are precluded from taking place on data being obtained until the inhibit situation subsides.

To compute ventilation in milliliters per minute, the area under the flow waveform, which is shaded in waveform A of FIG. 4, is integrated. On a breath by breath basis, the product of breathing frequency and volume therefore yields minute ventilation. However, when each of these volumes is added over a predetermined user selected time interval, the result is the average ventilation measured in liters per minute over a number of breaths. The system 10 of the present invention operates such that data remains current. When a new breath is taken, a frequency counter is incremented and the measured compenent attributable to the oldest breath which now lies outside of the user selected time interval is dropped off.

The manner in which the analog flow signal is processed to obtain the desired information content therefrom will be explained next.

The expiratory time ($T_E$) comprises the positive half-wave period of a pneumotach signal (waveform A) while the total time ($T_{TOT}$) is equal to the full wave time of the preceding breath. The tidal volume ($V_T$) is equal to the integrated value of the expiratory half cycle of the preceding breath and is represented by the shaded areas in waveform A. Using these variables, the ventilation measured in milliliters per minute and represented by the symbol $V_E$ comprises the volume multiplied by the breathing frequency over the last breath and can be expressed by equation 1 as follows:

$$V_E = \frac{(TV_1 + TV_2 + \ldots + TV_n)}{(TT_1 + TT_2 + \ldots + TT_n)} \cdot 60 \qquad \text{eq. 1}$$

where $(TT_1 + TT_2 + \ldots + TT_n)$ is greater than or equal to the user selected time interval, $TT_1$ is the oldest time and $TT_n$ is the newest time.

The waveform analyzer 30 functions to eliminate from these computations erratic samples representative of abnormal breathing episodes. Specifically, for any given breath to be considered valid by the system hardware, the tidal volume ($V_T$) or total expiratory volume for that given breath must exceed a minimum $V_T$ value established by the operator as a constant. When the total time sums exceed the user selected time interval, then the volume and time for the oldest breath are dropped from computations and the latest volume and time are added in. In this fashion, the data sampled by the waveform analyzer 30 and used for establishing the ventilation factor, $V_E$, is maintained on a current basis.

To obtain the desired $CO_2$ end tidal concentration, the waveform analyzer operates upon the signal output from the $CO_2$ analyzer 26 by summing the peak values of the impulses (waveform "B") over the same user selected time interval. By multiplying the phase aligned instantaneous flow and instantaneous $CO_2$ concentration, an integrated weighted average, representing volume of $CO_2$ expired ($VCO_2$) can be obtained.

In a similar fashion, the waveform analyzer operates on the $O_2$ signal, waveform "C", by summing the peak values of the wave over the user selected time interval. Then by multiplying the phase aligned instantaneous flow and instantaneous $O_2$ concentration, an integrated weighted average, representing volume of $O_2$ expired ($VO_2$) can be determined.

Upon receipt of an appropriate command signal from the host CPU 40 of FIG. 3, the waveform analyzer 30 will be made to sequentially sample the input channels 1–4 to feed in the flow, $CO_2$, $O_2$, and heart rate information. In addition, channels 5–8, optionally may be active in receiving information from a cycle ergometer, ear oximeter, etc. During the transmission and conversion operations, the processor in the waveform analyzer 30 can simultaneously be performing computations on previously received data and, in this fashion, computations and data transmissions may take place in an overlapped fashion. Data flowing from and to the host computer 40 is preferably encoded as a 7 bit ASCII code and transmission rates may be 2400 baud which is compatible with the well-recognized communications protocols for digital transmission systems.

The waveform analyzer 30 utilized in the system 10 of the present invention includes a microprocessor which is programmed to carry out a plurality of functions as will now be described with the aid of the flowcharts of FIGS. 5a through 5i.

Figure 5A:
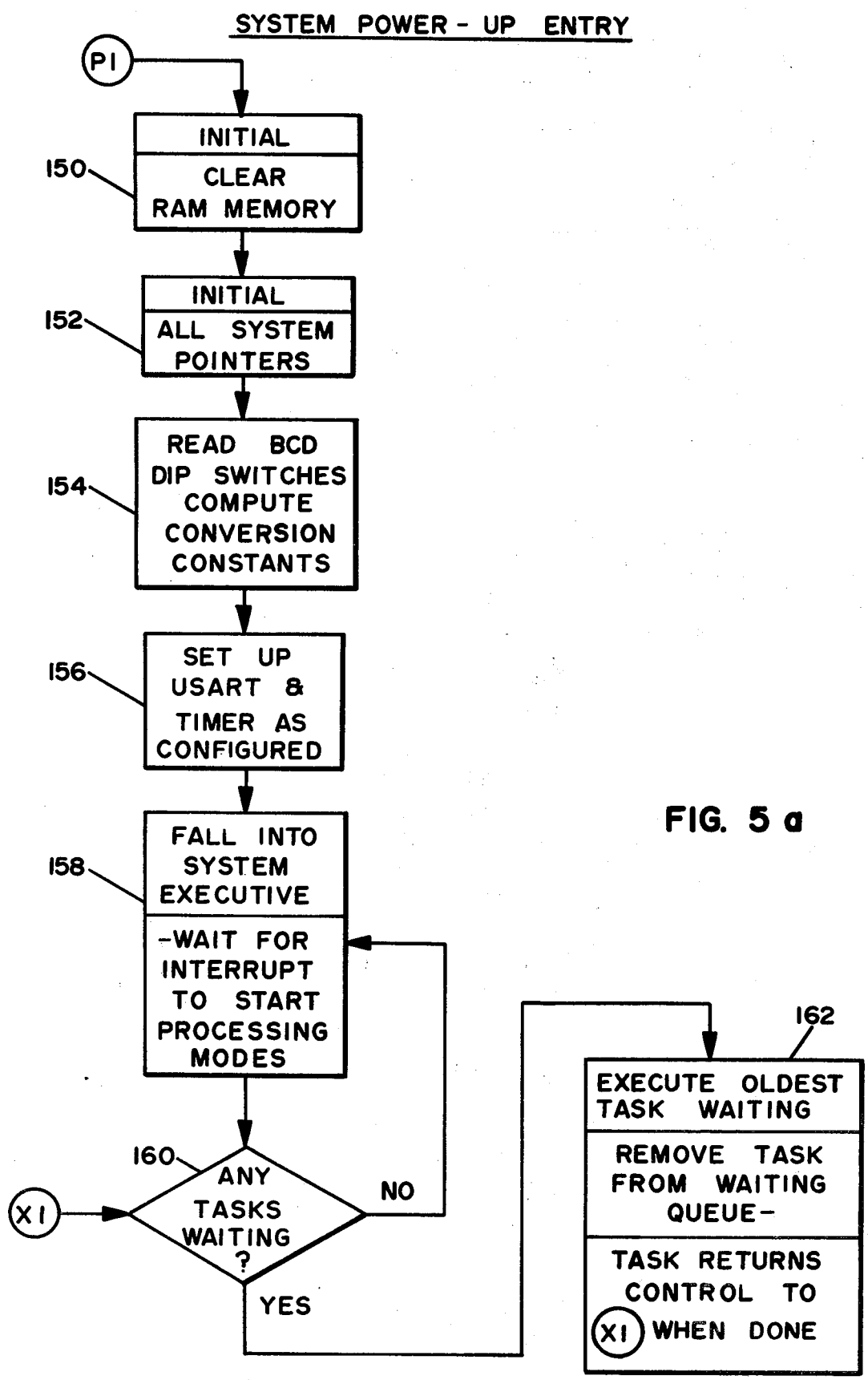
FIGS. 5a through 5i illustrate flow charts for the microprocessor based waveform analyzer of FIGS. 2 and 3; and, FIG. 6 illustrates one of the representative printouts of the system.

FIG. 5a is a flow chart for the operations performed upon system power-up. The microprocessor of the waveform analyzer 30 is interrupt driven, following the initialization upon power-up, all tasks are designed to return control to the system executive when they have been completed. Thus, as indicated in FIG. 5a, upon initialization, the microprocessor's RAM memory is cleared (block 150) and all of the address counters and stack pointers are initialized (block 152). Next, the microprocessor causes certain conversion constants which had been entered by manually operated DIP switches to be entered under program control into memory 154. The system's communication algorithm, termed USART, is initiated in a manner known to those familiar with the Intel 8085 microprocessor, this operation being represented by block 156 in the figure.

The system then enters the executive stream and waits for the first interrupt to occur whereby one of the various processing modes can be initiated. This operation is represented by block 158 in FIG. 5a. The decision block 160 provides the means whereby the microprocessor can determine whether any tasks are waiting to be processed. If so, the microprocessor handles them on a first-in, first-out basis as suggested by block 162. Upon completion of this oldest task, the control returns to entry point XI and if no other tasks are waiting, the executive sits in an idle mode waiting for the next interrupt to occur.

Figure 5B:
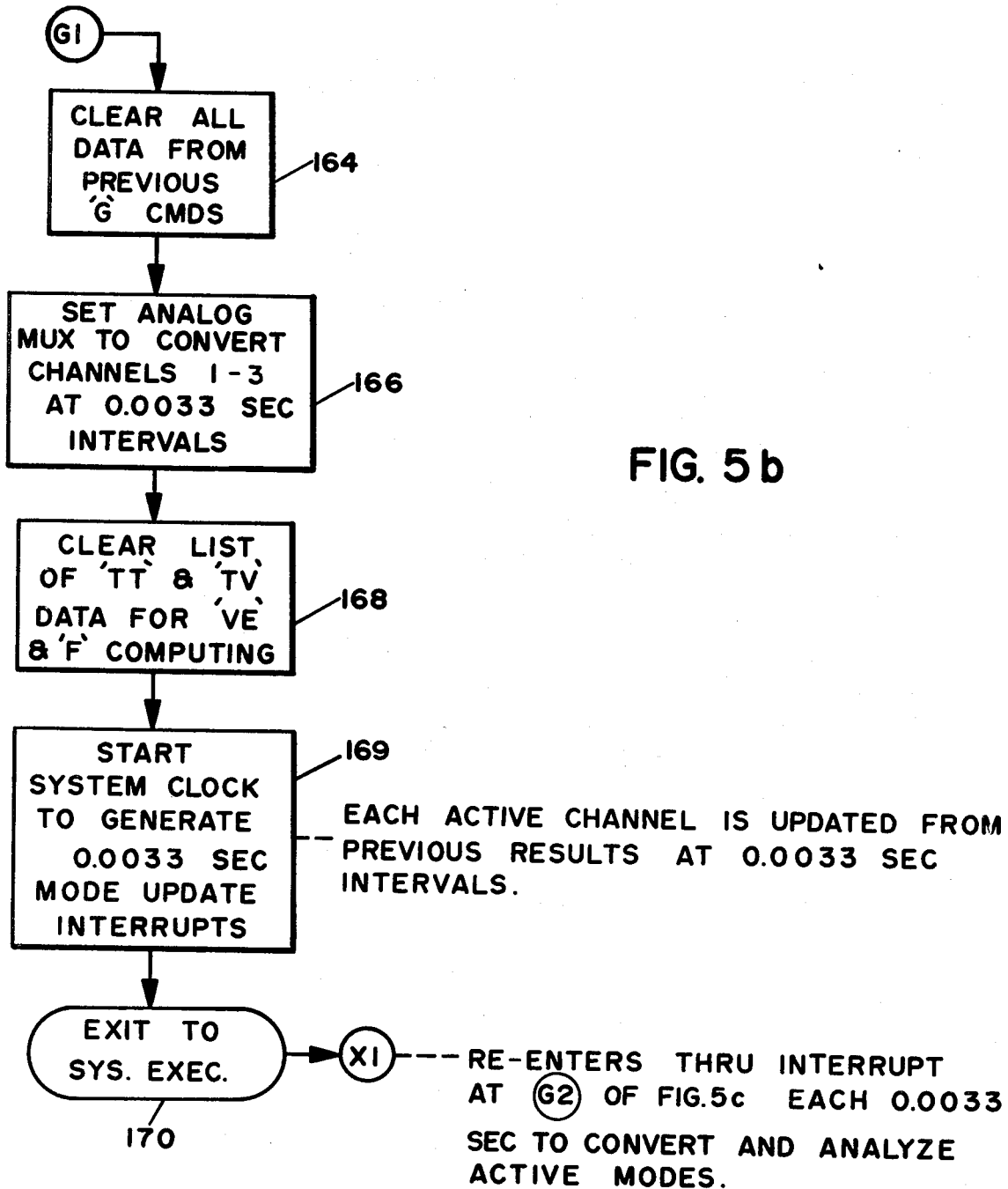

Data from the various sensors 14, 24, 26 and 28 of FIG. 2 are transferred into the waveform analyzer 30 under control of the so-called "G-command." The flow chart relating to the G-Command" is set forth in FIG. 5b. With reference to this figure, when the waveform analyzer receives the G-Command from the computer, it causes the waveform analyzer's microprocessor to clear all data from a previous command (block 164) and the analog multiplexer 54 of A/D converter of FIG. 3 are set to sample each of the channels 1-4 at a rate of approximately 100 times per second (block 166). Following that, the parameters of total times (TT) and tidal volume (TV) for computing ventilatory response (VE) and breath frequency (f) from a previous iteration are cleared. This is represented by block 168 in FIG. 5B. Next, the system clock is initiated such that mode update interrupt signals are outputted at about 100 samples per second and each active channel is updated from its previous result at the same 100 samples per second. Control is then returned to the system executive at entry point XI at block 170. The G-Command is reentered through an interrupt occurring each millisecond, the entry point being at G2 in the flow chart of FIG. 5C.

Figure 5C:
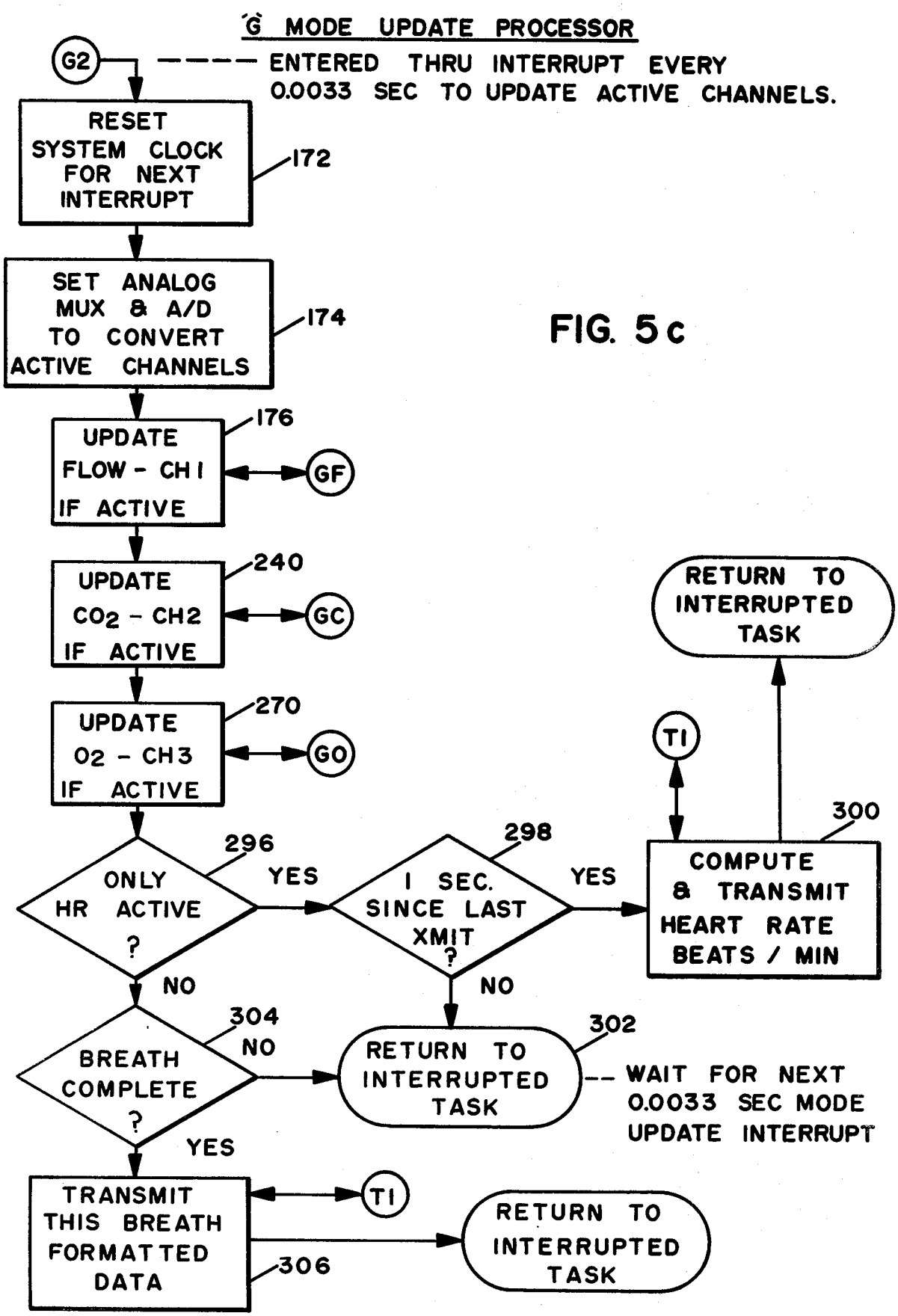

FIG. 5C shows that following entry, the system clock is reset readying it for receipt of a subsequent interrupt. Also, the analog multiplexer 54 and A/D converter 60 are conditioned to begin converting the data received on the active ones of the channels 1-4. These operations are represented by blocks 172 and 174, respectively. As previously described, channel 1 is arranged to receive flow information via the pneumotach 14 through carrier/demodulator 20. Channel 2 receives data from the $CO_2$ analyzer 26, while channel 3 is connected to receive data relating to oxygen concentration from the $O_2$ analyzer 24. Channel 4 is connected to receive heart rate data for an ECG 28.

Figure 5D:
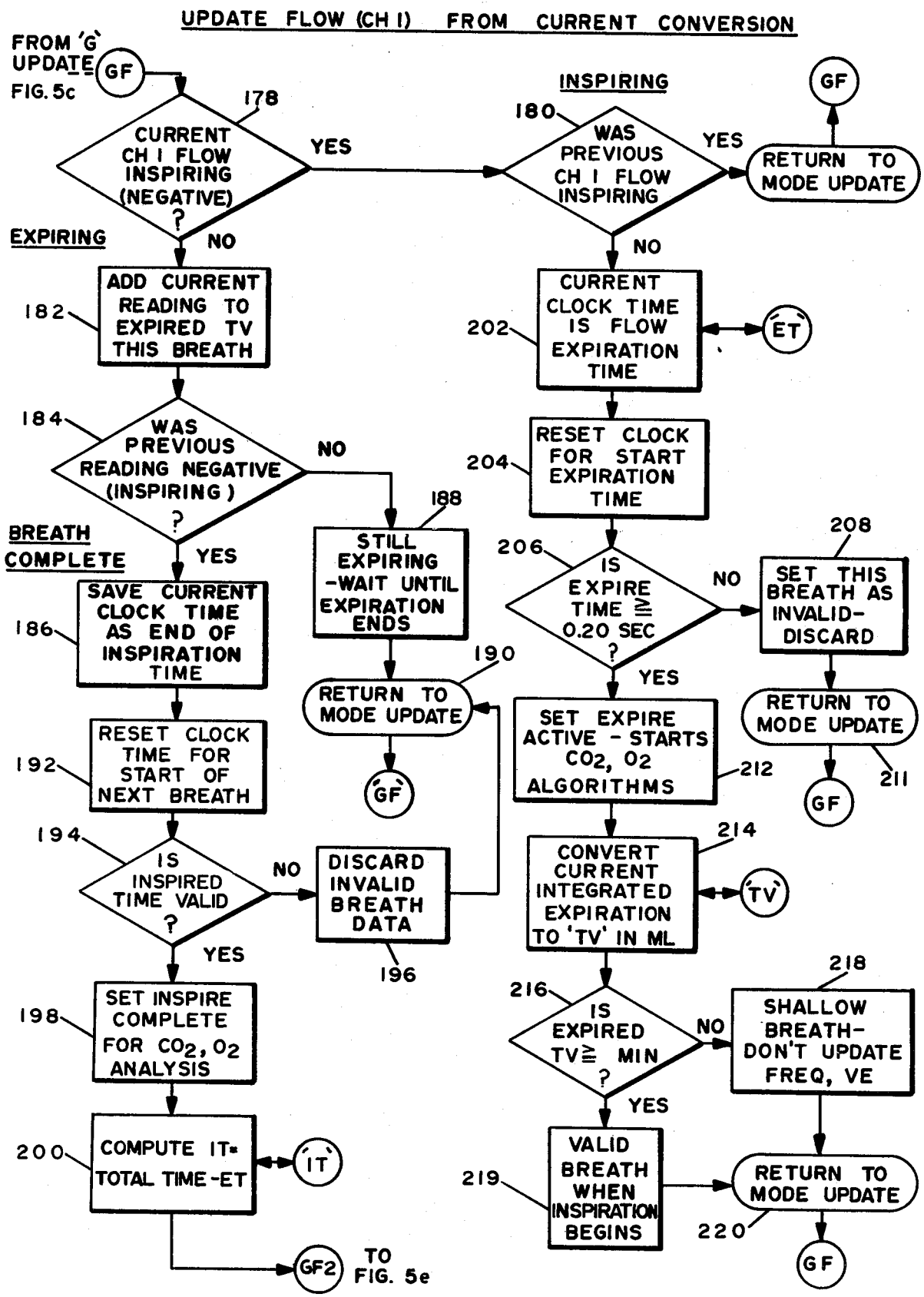
Figure 5E:
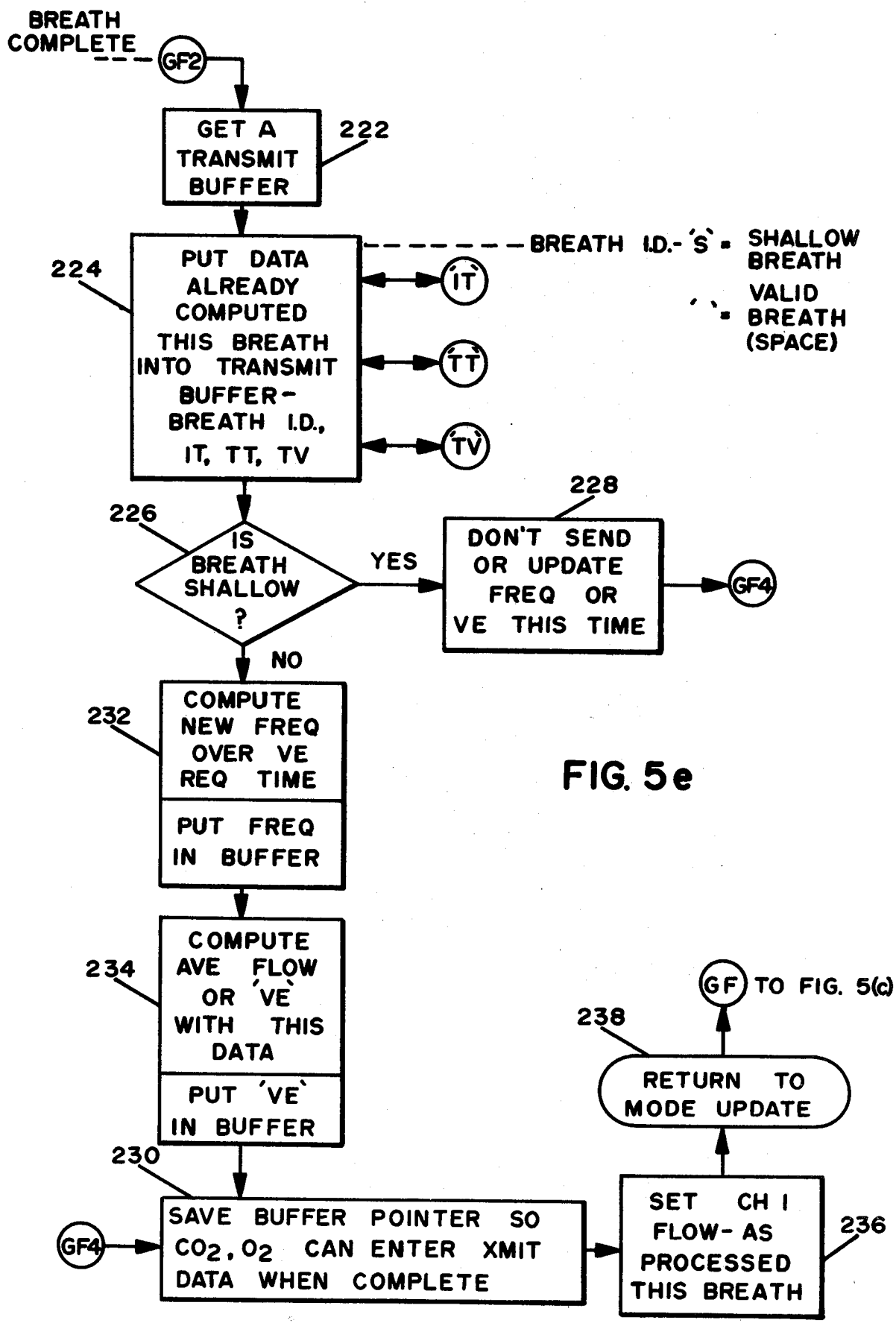

Assuming that channel 1 is active so that the flow information is to be updated, as is indicated by the block 176, the software exits to a flow conversion routine which is represented by the flow charts of FIGS. 5d and 5e. Thus, leaving the flow chart of FIG. 5c momentarily, consideration will next be given to the operations taking place in the flow conversion process.

FIG. 5d shows that control enters at the point labeled GF and at decision block 178 a determination is made whether the instantaneous data from the pneumotach 14 is representative of the inspiration portion of a complete respiratory cycle. If the waveform is negative, indicating inspiratory flow, the system follows the "Yes" output of block 178 and a determination is made whether the previous sample at channel 1 was indicative of inspiratory flow at block 180. If so, the control is looped back to the entry point GF and this sampling process is continued until the sample becomes positive, indicating the onset of an expiratory half-cycle. When this occurs, control exits the "No" path from decision block 178 and, as represented by block 182, the current reading is added to the expired tidal volume (TV) for this breath. Next, at decision block 184, a test is made as to whether the previous reading had been negative. Under the assumed conditions it had been and, hence, the processor's current clock time is stored to later indicate the end of the inspiration time, all as represented by block 186. If the previous reading on channel 1 had still been positive, indicative that the expiration half-cycle had not been completed and the subject was still expiring, the operations designated by blocks 188 and 190 comprise a feedback path to the entry point of the decision block 178. Following the output from block 186, then, the block 192 in the flow chart of FIG. 5d indicates that the clock time is reset to initiate the start time of the next breath.

Next, the expiration time portion of the cycle is compared to a predetermined constant set into the system by DIP (dual inline package) switches on the front panel of the waveform analyzer 30 and if the expiration time is less than the preset time, it is determined to be an invalid breath and the data relating to that internal is discarded. These operations are represented by the decision blocks 194 and 196, the output of this latter block being again routed so as to reinitiate the flow update algorithm by entering at the point GF. As was indicated earlier, an invalid breath may occur due to coughing or some other respiratory disturbance. The system of the present invention is thus able to discriminate against such irregular sampling intervals so that it cannot cause erroneous data to be processed.

Assuming that the expired time interval is indicative of a valid breath, a flag indicative that the expiratory cycle has been completed is set, this flag being utilized by the $CO_2$ and $O_2$ analysis routines, all as will be later described. This flag setting operation is represented by block 198. The microprocessor in the waveform analyzer then substracts the expiratory time from the total time to get inspiration time, IT, for the breath (block 200).

The explanation of the flow chart of FIG. 5d to this point has assumed that the expiratory cycle was being sampled. At the onset of an inspiration cycle, control exits the "No" path from the decision block 180 and operation 202 is performed whereby the current clock time is recorded as being the end of the expiratory cycle. The manner in which this piece of information is utilized is now described in more detail.

As represented by block 204, the system clock is reset to reflect the start of the expiration time. Again, at decision block 206 a test is made to determine whether the previous expiratory time was greater than or equal to 0.2 seconds. If not, that breath sample is rejected as invalid and control is returned to the entry point GF of block 178. Reference is made to blocks 208 and 210 of FIG. 5d. However, if the test criteria for decision block 206 is passed, the "inspire active" flag is set and the $CO_2$ and $O_2$ algorithms yet to be described are initiated. This operation is represented by the block 212 in FIG. 5d.

Next, as is indicated by block 214, the microprocessor in the waveform analyzer 30 functions to integrate the flow curve over the expiratory time interval to generate the tidal volume (TV) factor. At decision block 216 a test is made to determine whether the expired tidal volume is greater than or equal to the preset lower limit tidal volume and, if not, the sample is rejected as invalid such as a shallow breath and the computed value is not used to update the frequency and ventilation factors. Instead, control is again returned to the beginning of the "update flow" algorithm as represented by the blocks 218 and 220. However, if the expired tidal volume is greater than or equal to the preset lower limit tidal volume, the sampled breath is valid and at the begining of the inspiratory cycle control is again returned to the entry point of decision block 178.

FIG. 5e shows that the flow chart indicates the ensuing operations following the completion of the operation represented by block 200 in FIG. 5d. Specifically, once a breath sample is complete, a storage buffer is assigned, as represented by block 222, and the data to be transmitted from the waveform analyzer to the computer is assembled in that storage buffer. First, a breath I.D. indicative of a shallow breath or a valid breath is entered into the transmit buffer as is the inspiratory time, the total time, and the tidal volume factors, these operations being represented by block 224 in FIG. 5e. If a short breath is involved, the test block 226 routes control such that the assembled data is not sent but, instead, the same buffer area is reserved for later use by the $CO_2$ and $O_2$ sampling routines, this being represented by blocks 228 and 230 in FIG. 5e.

Assuming that the breath sample meets established criteria, the decision block 226 will route control such that the next operation, represented by block 232, will take place. That is, a new breath frequency value will be computed by multiplying 60 times the number of total time samples (TT) used and dividing that product by the sum of the total times of breaths obtained in a user selected time interval. Expressed mathematically:

$$F = \frac{60 \times N}{TT_1 + TT_2 + \ldots + TT_n}$$

In the above formula, $TT_1$ is the total time of the oldest breath in the sampling interval and $TT_n$ is the newest or most current total time of a breath sample.

After this computed value is stored in the selected transmit buffer, the next operation for the waveform analyzer microprocessor is to compute ventilation, all as represented by block 234 in FIG. 5e. The computed value is also placed in the transmit buffer at a desired location so that once transmitted to the receiving computer, the computer will recognize the data at that location as being related to the ventilation parameter.

Following the operation previously described in connection with block 230, the waveform analyzer sets a flag indicating that the flow update operation has been completed and that control may be returned to block 176 in FIG. 5c. These steps are represented by the blocks labeled 236 and 238 in the flow diagram of FIG. 5e.

Once control is returned to the "G-Mode Update Processor" routine, the next sequential step is represented by the block 240 in FIG. 5c. This block routes control to the "Update $CO_2$" routine set forth in the flow charts of FIGS. 5f and 5g.

Figure 5F:
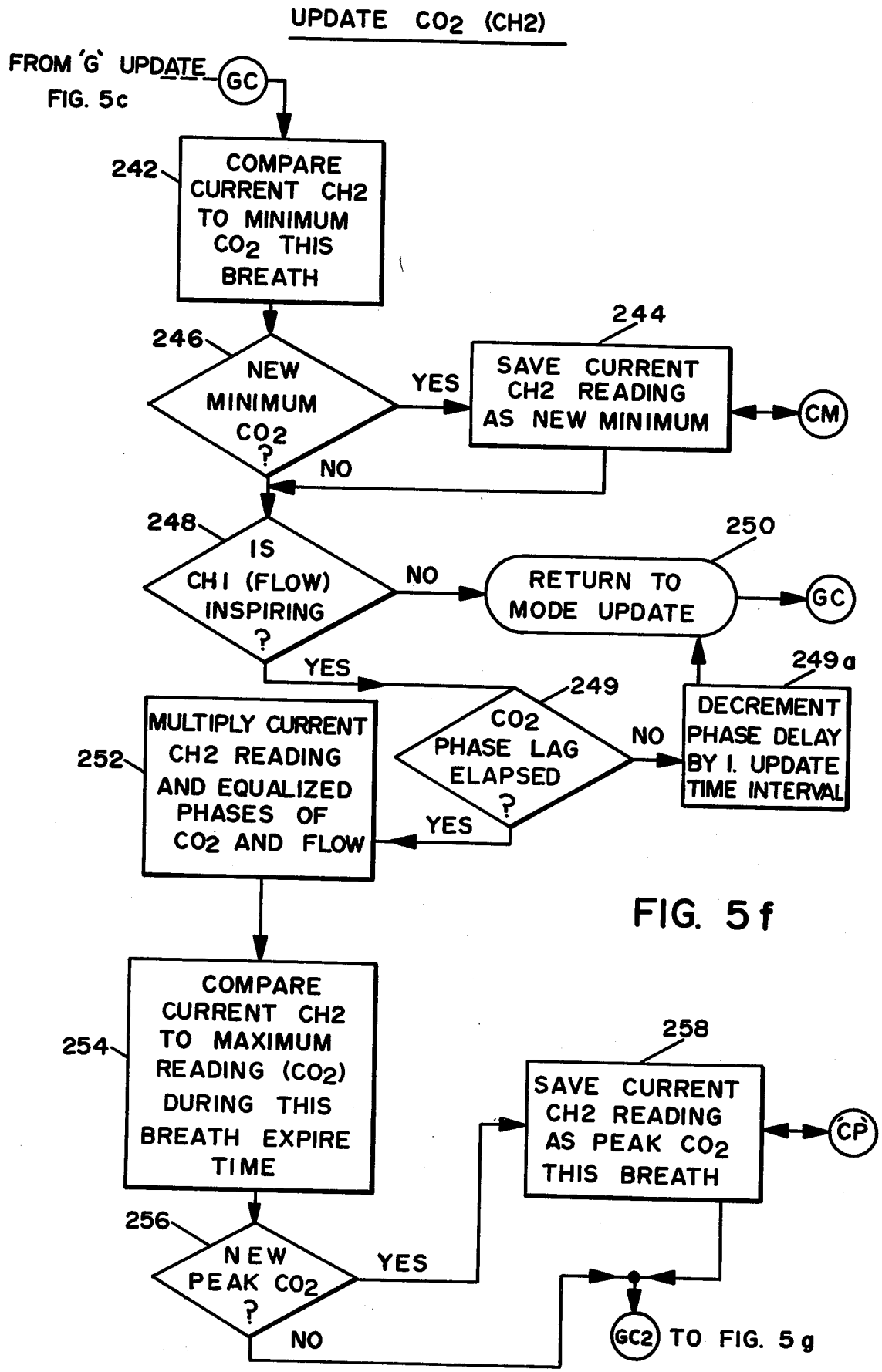

Once control passes to the "Update $CO_2$" routine, the first step to occur, represented by block 242 in FIG. 5f, is that a comparison is made between the current amplitude sample of the output from the analyzer 26 to the minimum amplitude from that device for the particular breath in question. If the current reading is less than the previous minimum reading that new reading is stored as the new "minimum" value block 244. If the test represented by block 246 reveals that the current reading exceeds a previous minimum or following the storage of the new minimum value, a subsequent test is conducted represented by decision block 248, and, again, the flow signal on Channel 1 is sampled to determine whether it is negative, indicative that the patient is in the inspiration portion of a breathing cycle. If not inspiring, control is returned to the input point of block 242 as represented by the symbol 250 in FIG. 5f. This sequencing continues until the test at decision block 248 reveals that the patient has begun an expiration cycle, and at this point, after allowing for the phase lag, the current channel 2 reading is multiplied by the instaneous expired flow corresponding to that time and is integrated by block 252. The phase log itself is introduced by providing a preset counter which is decremented at a fixed rate (block 249a) with a test being made on each iteration as to whether the prescribed time period had elapsed (block 249). Then, the current $CO_2$ level at the time of sampling is compared to the maximum reading of $CO_2$ level during the expiration cycle of the breath in progress block 254. Next, the test represented by decision block 256 is carried out whereby a determination is made whether the current $CO_2$ reading comprises a new peak. If so, this current reading is stored as indicative of the peak $CO_2$ value for the breath in question. This operation is represented by block 258 in FIG. 5f.

Figure 5G:
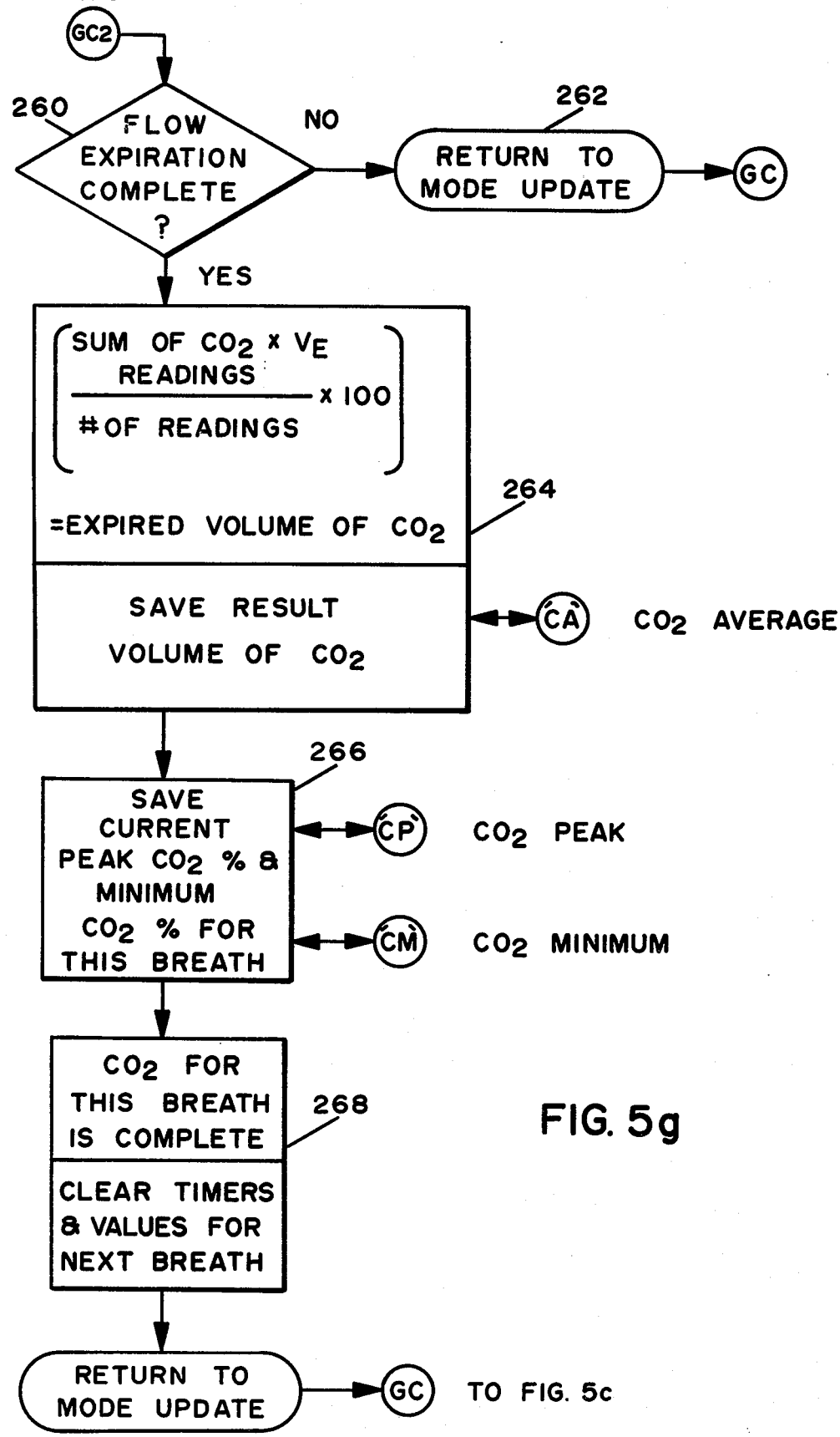

If the current $CO_2$ level does not comprise a new peak or if it does and that peak reading is stored, control is directed to the decision block 260 in FIG. 5g. Here, a test is made to determine whether the flow expiration has been completed. If not, control is returned to the entry point of the block 242 in FIG. 5f as represented by the operation 262. Assuming the expiration cycle is complete, the waveform analyzer's microprocessor is made to compute the volume of $CO_2$ during the expiratory cycle. The resulting parameter is stored and comprises the weighted average expired of $CO_2$ volume. Being an electronically stored parameter, the need for a holding chamber to retain the expired gas samples for a later batch-type analysis, as in the prior art, is obviated. These operations are identified by block 264 in FIG. 5g.

If the results of the tests at decision blocks 246 and 256 had been negative such that the minimum $CO_2$ and peak $CO_2$ had not been previously stored, these values are now stored as represented by the block 266. The $CO_2$ parameters for this particular breath have then been completed and the software causes the various timers and previously computed values in the operational registers to be cleared so as to prepare the system for sampling the next succeeding breath. These operations are represented by the block 268 in FIG. 5g. Control then reverts to the beginning of the "Update $CO_2$" sequence at block 242 in FIG. 5f.

Referring again to FIG. 5c, the "G-Mode Update" algorithm, following completion of the "Update $CO_2$ sequence, control reverts to the "Update $O_2$" operation represented by block 270. Control exits the block 270 to the sequence represented by the further flow diagrams of FIGS. 5h and 5i. This is the so-called "Update $O_2$"

sequence and as a first step, represented by block 272, a comparison is made between the instant $O_2$ amplitude on channel 3 and the maximum reading which had been obtained for this particular breath. At decision block 274, a determination is made as to whether the current sample exceeded any previous sample and, if so, the current reading is stored away as a new peak $O_2$ value block 276. Following this operation, or following immediately after the determination is made that the new sample is not a peak value, the signal on channel 1 is again sampled to determine whether it is positive, indicative of an expiratory cycle. This test is indicated by decision block 278 in FIG. 5h and if the test proves negative, a jump, represented by block 279b, is made back to the original compare step 272. If an expiratory cycle is in progress and the phase lag has been accounted for, the current amplitude reading on channel 3 is multiplied by the instaneous expired flow corresponding to that time and is integrated for the current breath as represented by block 280. If the phase lag is not accounted for at block 279, then the phase lag is decremented by block 279a which goes back to block 279b.

Figure 5H:
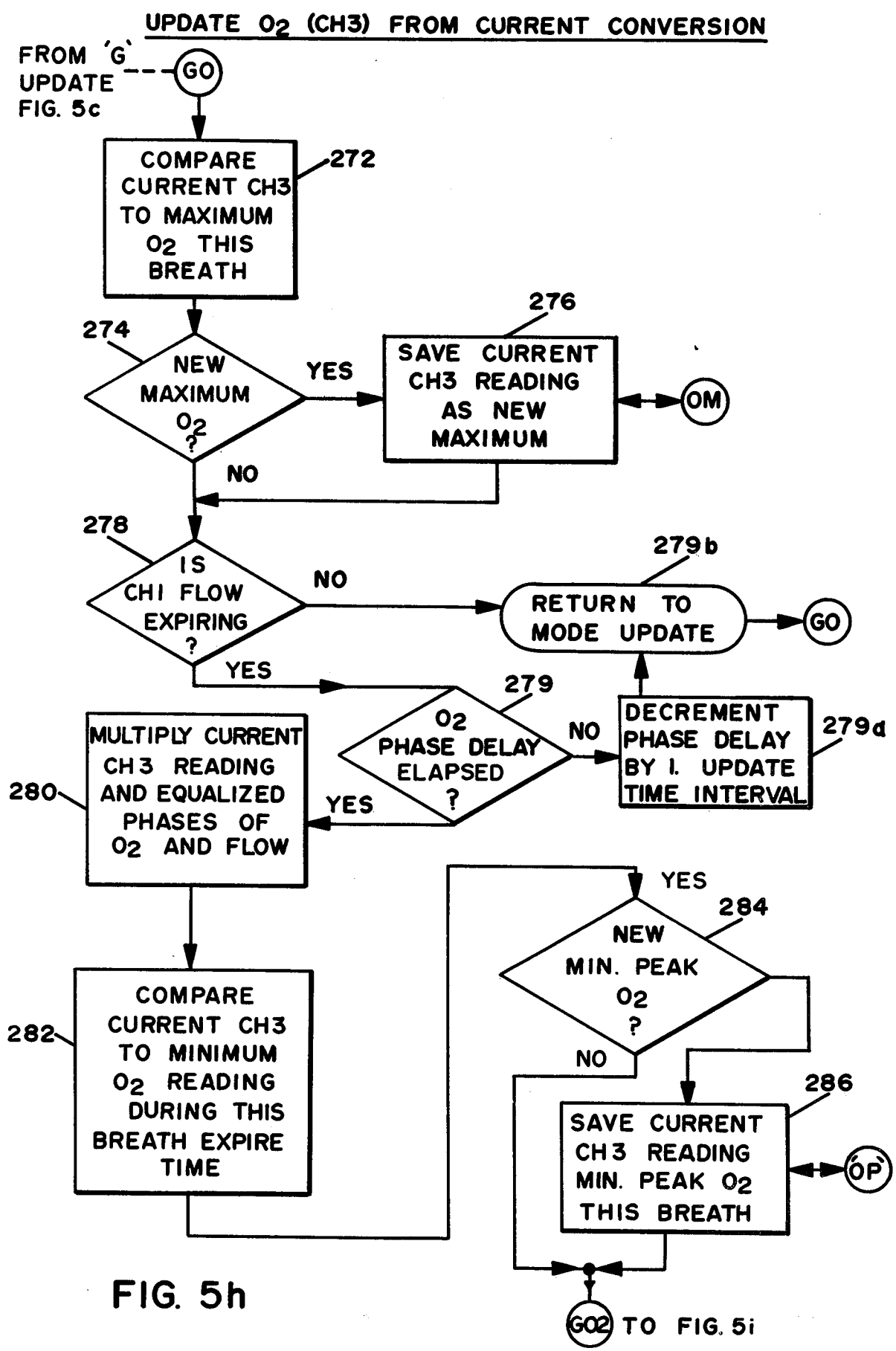

In FIG. 5h, the current reading taken from the $O_2$ channel is compared to the minimum $O_2$ reading obtained during the expiration time of the current breath block 282. Block 284 symbolizes the steps to be taken as a result of that comparison. Specifically, if the current channel 3 reading is less than any previous reading taken during that same breath interval, it is considered to be the new minimum peak and that value is stored temporarily as represented by block 286.

Figure 5I:
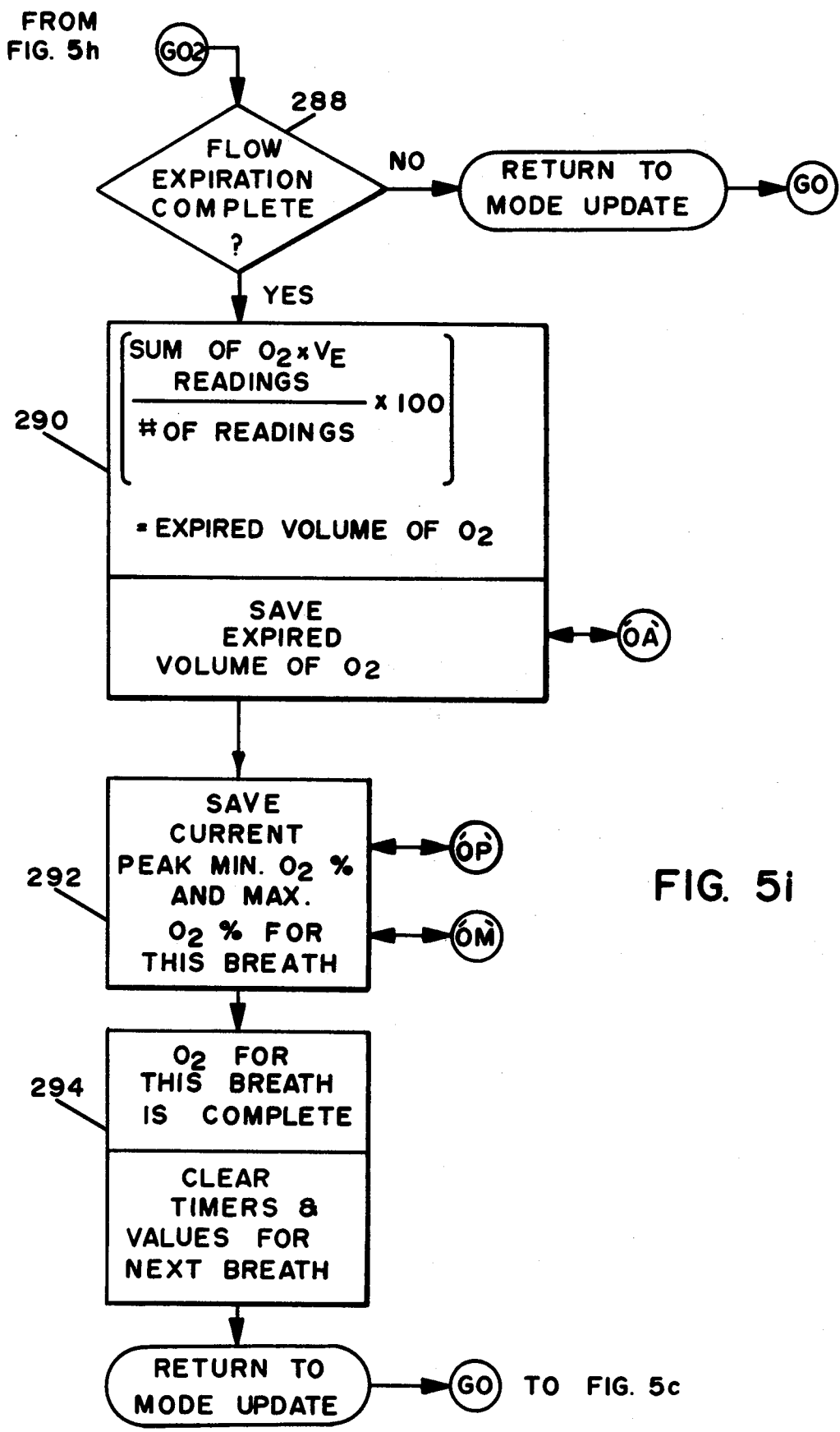

Following the storing step, control passes to the flow chart entry point GO2 on FIG. 5i. As such, in decision block 288 a decision is made whether the expiratory cycle is complete and, if not, the sequence jumps back to the entry point GO at block 272 in FIG. 5h. However, if the expiratory flow has been completed, the next step is to compute the volume of $O_2$ expired by integrating the products obtained in block 200 over the expiratory cycle and thereby alleviating the need for a mixing chamber. The resulting parameter is the weighted average of $O_2$ volume and the various operations mentioned are represented by the block 290. Next, if the maximum $O_2$ value and the peak $O_2$ values had not previously been stored as indicated by operations 276 and 286, these values are now stored in block 292 which completes the $O_2$ analysis for this particular breath.

At this time, then, the various timers and counters used in the process are cleared or otherwise initiated for repeating the same functions on subsequent breaths. This operation is identified by block 294 in FIG. 5i. Upon completion of that step, control is returned to block 270 in FIG. 5c.

With continued reference to FIG. 5c, if none of the flags GF, GC or GO are active, the heart rate HR on channel 4 is next considered. Specifically, a test is made at decision block 296 to determine if only the HR flag is indicating activity. If it is the only active channel requiring update, a further test indicated by block 298 is made to determine whether one second has elapsed since a data stream was last transmitted from the waveform analyzer 30 to the computer 40. If more than one second has elapsed since the previous heart rate data had been sent, the operation symbolized by block 300 is performed such that a new heart rate value in beats/minute is computed and transmitted. Control then returns to the task which had been interrupted to accomplish the foregoing computation and transmission.

If the interrupt had occurred earlier than one second after the preceding heart rate information had been transmitted, a return to the interrupted task takes place immediately without a re-computation and transmission. This is indicated by the operation block 302 in FIG. 5c. Similarly, if the test 296 reveals that other than HR flags are active, a further test is made at 304 to determine whether a breath has been completed. Again, if not, an immediate return to the interrupted task takes place. If, however, the breath had been completed the entire string of data for that particular breath which had previously been formatted is transmitted block 306 to the receiving computer.

The system 10 is capable of accessing and storing forty parameter for each breath. Some of the parameters are user input as indicated by a "u" in parentheses.

User parameters inputted—
1. Speed or workload; i.e. treadmill or ergometer (u).
2. Elevation or power (u)—i.e., ergometer or treadmill
3. $\dot{V}E$ ATPS—(ambient atmosphere, temperature and pressure, saturated)
4. True $O_2$
5. True $CO_2$
6. Respiratory frequency
7. Cardiac frequency
8. $O_2$ Saturation
9. $\dot{V}E$ BTPS (Body temperature, Pressure, Saturated)
10. VE BTPS—Tidal volume at body conditions.
11. $\dot{V}O_2$—$O_2$ uptake
12. $\dot{V}CO_2$—$CO_2$ output
13. R—respiratory exchange ratio
14. $O_2$ Pulse
15. $\dot{V}E/\dot{V}CO_2$
16. $PO_2$ (u)—arterial $O_2$
17. $CO_2$ (u)—arterial $CO_2$
18. pH (u)
19. Base Excess (u)
20. A—$aPO_2$
21. $V_D/V_T$
22. $O_2/KG$
23. $VE/VO_2$
24. PET $CO_2$—Partial Pressure of end tidal $CO_2$
25. Custom Location—open
26. PET $O_2$—Partial Pressure of end tidal $O_2$
27. Systolic Pressure (either user input or read by wave form analyzer)
28. Diastolic Pressure (either user input or read by wave form analyzer.
29. Relative Time
30. Workload
31. $\dot{V}E$ STPD (Standard temperature, pressure, dry)
32. VT/VC
33. METS
34. Inspiratory Time
35. Total Time of last breath
36. Inspiratory Base Line $O_2$
37. Inspiratory Base Line $CO_2$
38. Custom variables VT/TI
39. Custom variables TI/TT
40. Interval number The system 10 accesses, computes, and stores 22 parameters for each breath by breath for subsequent plotting as these dynamic values are the most meaningful in terms of plotting. The plotting on a CRT or printer can be limited to a selected interval with minimum and maximum values, or from zero to a predetermined value.

The dynamic values capable of being plotted are delineated below:
1. VT (tidal volume)
2. t (seconds)
3. Workload (kpm)
4. VT/VC (%)
5. V̇E (minute ventilation)
6. TRUE $O_2$ (V̇$O_2$/V̇E STPD)
7. TRUE $CO_2$ (V̇$CO_2$/V̇E STPD)
8. Sa$O_2$ ($O_2$ saturation %)
9. V̇$O_2$ ($O_2$ consumption ml/min)
10. V̇$CO_2$ ($CO_2$ production ml/min)
11. Heart rate
12. R (respiratory exchange ratio)
13. $O_2$ pulse (ml/bpm)
14. V̇E/V̇$CO_2$ ($CO_2$ ventilatory equiv)
15. VE/V$O_2$ ($O_2$ ventilatory equiv)
16. $O_2$/kg (ml $O_2$/kg/min)
17. Systolic (mmHg)
18. Diastolic (mmHg)
19. METS
20. PET$O_2$ (end tidal $O_2$ %)
21. PET$CO_2$ (end tidal $CO_2$ %)
22. Respiratory Rate FIG. 6 is illustrative of a printout in tabular form of an individual's dynamic parameters and is representative of measured parameters during stress testing. Proceeding from left to right in FIG. 6, the parameters listed are delineated below:
1. Relative time "dependent on time interval"
2. Tidal volume
3. Respiratory rate
4. Expired Ventilation
5. Partial Pressure—End tidal $O_2$
6. Partial Pressure—End tidal $CO_2$
7. $O_2$ uptake
8. $CO_2$ output
9. Respiratory quotient ($CO_2$/$O_2$)
10. Ventilation equivalent $O_2$
11. Ventilation equivalent $CO_2$
12. Heart Rate
13. $O_2$ Pulse/Heart Rate
14. Ear Oximeter The waveform analyzer 30 provides for detecting the baseline threshold as represented by the expired flow of waveform "A" in FIG. 4. This threshold provides for the real time, breath-by-breath analysis of an individual's parameters. The waveform analyzer 30 further stores the expired flow values while incrementing and accounting for the phase lag of the $CO_2$ signal and the $O_2$ signal as illustrated in waveforms "B" and "C" in FIG. 4. These three values along with the ECG of the waveform "D" of FIG. 4 provides the necessary input parameters to the waveform analyzer 30 providing for the calculations and output of the CPU 40. The waveform analyzer 30 provides the real time analysis of each breath as set forth in the flow charts of FIG. 5 inclusive.

The system 10 provides for distributed processing of the signals through the use of a microprocessor based waveform analyzer 30 having means for converting the received analog signals and the use of a host processor for controlling the display and printing functions to digital signals. The system 10 also provides for instanteous display of an individual's paremeters after each breath and before the next breath.

The sample tubes and flow measuring module 16 are movable, being positioned by an adjustable spring arm linkage arrangement.

The waveform analyzer 30 preferably includes an LED display window 30a for displaying the tidal volume, end tidal $CO_2$, entidal $O_2$, and heart rate.

Various modifications can be made to the present invention without departing from the scope thereof. A/D converter connected to a flow volume PFT Lab can connect to the CPU 40 as well as a 32 character A/N Display can connect to the waveform analyzer 30. While the CPU 40 has been disclosed as being dedicated to the system 10, the CPU 40 can also be used to perform other numerical calculations related or unrelated to the system 10 for best time sharing of the CPU 40 as deemed necessary by the individual's user.

The system 10 can also be utilized in other types of clinical applications besides the applications previously disclosed. The studies could include nutritional studies, caloric requirement studies, etc. While the system 10 has been disclosed as a flexible dedicated system, it can also be utilized in a nondedicated mode of operation.

The CPU 40, keyboard 44 and and plotting printer can be incorporated in the rack 12 where the CPU 40 can be positioned in the lower panel, and an upper panel can be provided for a polycarbonate overlay keyboard in lieu of the keyboard 44. A plotting printer can also be provided in the rack 12 thereby providing a single integral rack unit for the system 10.

It is important to note that the system 10 monitors and analyzes the first breaths of exercise for evaluation of the metabolic response to exercise e.g. the increase in cardiac output which is attributable to the increase in stroke volume.

The system 10 further calibrates for phase delay of the analog signals of the input parameter signals on a real time basis which is unique in operation to the system 10.

Having thus described the invention, what is claimed is:

1. A cardiopulmonary performance testing and display system comprising in combination:
    (a) a mouthpiece member adapted for placement in a subject's mouth, said mouthpiece member including means for generating a first analog electrical signal proportional to inspiratory and expiratory gas flow by said subject;
    (b) first gas analyzing means coupled to said mouthpiece member for producing a second analog electrical signal proportional to the level of carbon dioxide in said expiratory gas flow;
    (c) second gas analyzing means coupled to said mouthpiece member for producing a third analog electrical signal proportional to the level of oxygen in said expiratory gas flow;
    (d) waveform analyzer means including
        (1) a first computer programmed to perform arithmetic operations in accordance with a stored program of instructions;
        (2) means controlled by said computer means and connected to the first-named means, and said first and second gas analyzer means for sampling said first, second and third analog electrical signals in a predetermined sequence and converting said first, second and third analog electrical signals into digital quantities representative of said analog electrical signals during the sampling interval of each;

(3) means in said first computer for at least temporarily storing said digital quantities as operands for said arithmetic operations;

(e) means for displaying the results of said arithmetic operations;

(f) second computer means remote from said first microprocessor means connected in a controlling relationship to said means for displaying; and (g) means for transmitting said results of said arithmetic operations from said first computer means to said second computer means.

2. The cardiopulmonary performance testing and display system as in claim 1 and further including:

(a) means for generating a heart rate signal; and (b) means for coupling said heart rate signal to said means for sampling in said waveform analyzer means.

3. The cardiopulmonary performance testing and display system as in claim 1 and further including:

(a) means for applying further signals to said waveform analyzer means relating to workload being performed by said subject.

4. The cardiopulmonary performance testing and display system as in claim 1 wherein said means for sampling functions at a rate which is at least 100 times higher than the period of inspiratory flow or expiratory flow.

5. The cardiopulmonary performance testing and display system as in claim 1 wherein said results of said arithmetic operations are transmitted to said microprocessor means at a rate which permits said means for displaying to operate on a breath-by-breath basis.

6. The cardiopulmonary performance testing and display system as in claim 1 and further including:

(a) means for comparing the digital quantity representative of said first analog electrical signal with a predetermined reference quantity and excluding said digital quantity from being one of said operands upon failure of said digital quantity to compare to said reference quantity.

* * * * *

UNITED STATES PATENT AND TRADEMARK OFFICE
CERTIFICATE OF CORRECTION

PATENT NO. : 4,463,764
DATED : August 7, 1984
INVENTOR(S) : Stephen T. Anderson et al It is certified that error appears in the above-identified patent and that said Letters Patent are hereby corrected as shown below:

Column 16, Line 57, "computer programmed" should read -- computer means programmed --.

Column 16, Line 60, "said computer" should read -- said first computer --.

Column 17, Line 1, "computer for" should read -- computer means for --.

Column 17, Line 7, "microprocessor" should read -- computer --.

Signed and Sealed this

Sixteenth Day of April 1985

[SEAL]

Attest:

DONALD J. QUIGG

Attesting Officer     Acting Commissioner of Patents and Trademarks

UNITED STATES PATENT AND TRADEMARK OFFICE
CERTIFICATE OF CORRECTION

PATENT NO. : 4,463,764

DATED : August 7, 1984

INVENTOR(S) : Stephen T. Anderson, et al.

It is certified that error appears in the above-identified patent and that said Letters Patent is hereby corrected as shown below:

In the first column on the title page add the following immediately below the information by bracket [22]:

"Related U.S. Application Data
[63] Continuation-in-part of Serial No. 165,949,
July 3, 1980, abandoned."

In column 1, line 6, delete "relates to" and add the following in its place:

"is a continuation-in-part of".

Signed and Sealed this

Twenty-third Day of March, 1993

Attest:

STEPHEN G. KUNIN

*Attesting Officer*     *Acting Commissioner of Patents and Trademarks*